US011261145B2

(12) United States Patent
Schaefer et al.

(10) Patent No.: US 11,261,145 B2
(45) Date of Patent: Mar. 1, 2022

(54) PROCESS FOR PREPARING BROMOTRICHLOROMETHANE

(71) Applicant: BASF SE, Ludwigshafen am Rhein (DE)

(72) Inventors: Bernd Schaefer, Ludwigshafen (DE); Roland Goetz, Ludwigshafen (DE); Volker Hickmann, Ludwigshafen (DE); Volker Maywald, Ludwigshafen (DE); Daniel Saelinger, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 151 days.

(21) Appl. No.: 16/495,424

(22) PCT Filed: Mar. 12, 2018

(86) PCT No.: PCT/EP2018/055999
§ 371 (c)(1),
(2) Date: Sep. 19, 2019

(87) PCT Pub. No.: WO2018/172109
PCT Pub. Date: Sep. 27, 2018

(65) Prior Publication Data
US 2020/0071246 A1 Mar. 5, 2020

(30) Foreign Application Priority Data
Mar. 20, 2017 (EP) .................... 17161730

(51) Int. Cl.
C07C 17/10 (2006.01)
B01J 19/12 (2006.01)

(52) U.S. Cl.
CPC ............. C07C 17/10 (2013.01); B01J 19/123 (2013.01); B01J 19/127 (2013.01); B01J 2219/0877 (2013.01); B01J 2219/1203 (2013.01)

(58) Field of Classification Search
CPC ......... C07C 17/10; C07C 19/14; C07C 17/23; C07C 17/278; C07C 19/10; C07C 17/00; C07C 19/08; C07C 17/204; C07C 29/124; C07C 31/38; B01J 19/123; B01J 19/127; B01J 2219/0877; B01J 2219/1203; B01J 27/125; C07D 231/22; C07B 2200/13
See application file for complete search history.

(56) References Cited

U.S. PATENT DOCUMENTS

| 4,359,371 | A | 11/1982 | Bohm et al. |
| 10,118,882 | B2 | 11/2018 | Gebhardt et al. |
| 10,266,468 | B2 | 4/2019 | Wolf et al. |
| 10,266,469 | B2 | 4/2019 | Wolf et al. |
| 2018/0134641 | A1 | 5/2018 | Wolf et al. |
| 2018/0141917 | A1 | 5/2018 | Klauber et al. |
| 2018/0141924 | A1 | 5/2018 | Wolf et al. |
| 2019/0008162 | A1 | 1/2019 | Gockel et al. |
| 2019/0055200 | A1 | 2/2019 | Klauber et al. |
| 2019/0169108 | A1 | 6/2019 | Hickmann et al. |
| 2019/0263764 | A1 | 8/2019 | Rack et al. |
| 2019/0270710 | A1 | 9/2019 | Maywald et al. |

FOREIGN PATENT DOCUMENTS

| DE | 1259318 | B | 1/1968 |
| FR | 2356616 | A1 | 1/1978 |
| JP | S5353602 | A | 5/1978 |
| WO | WO-2016/180614 | A1 | 11/2016 |
| WO | WO-2016/180642 | A1 | 11/2016 |
| WO | WO-2016/180833 | A1 | 11/2016 |
| WO | WO-2016/202807 | A1 | 12/2016 |
| WO | WO-2017/025454 | A1 | 2/2017 |
| WO | WO-2017/032580 | A1 | 3/2017 |
| WO | WO-2017/102905 | A1 | 6/2017 |
| WO | WO-2017/133942 | A1 | 8/2017 |
| WO | WO-2017/144336 | A1 | 8/2017 |
| WO | WO-2017/144337 | A1 | 8/2017 |
| WO | WO-2017/162545 | A1 | 9/2017 |
| WO | WO-2017/207539 | A1 | 12/2017 |
| WO | WO-2017/215928 | A1 | 12/2017 |
| WO | WO-2017/215929 | A1 | 12/2017 |
| WO | WO-2018/015525 | A1 | 1/2018 |
| WO | WO-2018024820 | A1 | 2/2018 |
| WO | WO-2018/050518 | A1 | 3/2018 |
| WO | WO-2018/050792 | A1 | 3/2018 |
| WO | WO-2018/050793 | A1 | 3/2018 |
| WO | WO-2018/050794 | A1 | 3/2018 |
| WO | WO-2018/050795 | A1 | 3/2018 |
| WO | WO-2018/082964 | A1 | 5/2018 |
| WO | WO-2018/083040 | A1 | 5/2018 |
| WO | WO-2018/091338 | A1 | 5/2018 |

(Continued)

OTHER PUBLICATIONS

Tanner et al. "Free redical halogenation of deuteriochloroform", Canadian Journal of Chemistry 47, 4709 (1969), p. 4709-4711.*
Atherton, et al., "129. Studies on phosphorylation. Part III. Further observations on the reaction of phosphites with polyhalogen compounds in presence of bases and its application to the phosphorylation of alcohols", Journal of the Chemical Society (Resumed), Issue 0, 1947, pp. 674-678.
Barton, et al., "The functionalization of saturated hydrocarbons. Part 25. Ionic substitution reactions in GoAggIV chemistry: the formation of carbon-halogen bonds", Tetrahedron, vol. 50, Issue 1, Apr. 3, 1994, pp. 31-46.

(Continued)

Primary Examiner — Xiuyu Tai
(74) Attorney, Agent, or Firm — Marshall, Gerstein & Borun LLP

(57) ABSTRACT

The present invention relates to a process for preparing bromotrichloromethane comprising
a) providing bromine in chloroform; and
b) radiation of the resulting solution with light in the range of 350 to 550 nm, wherein said solution of bromine in chloroform is not radiated with radiation of a wavelength below 350 nm.

13 Claims, No Drawings

(56) References Cited

FOREIGN PATENT DOCUMENTS

| WO | WO-2018/095863 A1 | 5/2018 |
| --- | --- | --- |
| WO | WO-2018/114732 A1 | 6/2018 |
| WO | WO-2018/114733 A1 | 6/2018 |
| WO | WO-2018/141642 A1 | 8/2018 |
| WO | WO-2018/149676 A1 | 8/2018 |
| WO | WO-2018/172109 A1 | 9/2018 |

OTHER PUBLICATIONS

Bohlman, et al., "Reactions of Bromine with Carbon Tetrachloride and Tetrachloroethylene Following Neutron Capture and Isomeric Nuclear Transition", Journal of the American Chemical Society, vol. 64, Issue 6, Jun. 1, 1942, pp. 1342-1346.

Huyser, "The Photochemlcally Induced Reactions of Bromotrlchloromethane with Alkyl Aromatics", Journal of the American Chemical Society, vol. 82, Issue 2, Jan. 1, 1960, pp. 391-393.

European Search Report for EP Patent Application No. 17161730.1, dated May 17, 2017, 4 pages.

International Search Report and Written Opinion for PCT Patent Application No. PCT/EP2018/055999, dated Apr. 23, 2018.

Lecomte, et al., "Spectres infrarouges et spectres raman des chlorobromomethanes", Comptes rendus hebdomadaires des seances de l'academie des sciences, Gallica, Jan. 1, 1937, pp. 1927-1929.

Lehmann, et al., "Eine Einfache Darstellungsmethode für Bromtrichlormethan", Praktische Chemie, vol. 22, Issue 5-6, Dec. 1963, pp. 230-231.

Matsumoto, et al., "Detailed kinetic analysis of the radical polymerization of trans-4-tert-butylcyclohexyl methacrylate in benzene based on the rate constants determined by electron spin resonance spectroscopy", Macromolecules, vol. 27, Issue 20, Sep. 1, 1994, pp. 5863-5870.

Newman, et al., "The Use of Bromotrichloromethane in Chlorination Reactions", Synthesis, vol. 2, 2011, pp. 342-346.

Takahashi, et al., "A reagent-dependent highly chemoselective halogenation reaction of zirconacyclopentenes", Journal of the Chemical Society, Chemical Communications, Issue 6, 1994, pp. 747-748.

Willard, et al., "The Photobromination of Tetrachloroethylene and of Chloroform with Special Reference to the Effects of Oxygen" Journal of the American Chemical Society, vol. 57, Issue 11, Nov. 1, 1935, pp. 2240-2245.

\* cited by examiner

PROCESS FOR PREPARING BROMOTRICHLOROMETHANE

This application is a National Stage application of International Application No. PCT/EP2018/055999, filed Mar. 12, 2018. This application also claims priority under 35 U.S.C. § 119 to European Patent Application No. 17161730.1, filed Mar. 20, 2017.

The present invention relates to a process for preparing bromotrichloromethane comprising
  a) providing bromine in chloroform; and
  b) radiation of the resulting solution with light in the range of 350 to 550 nm,
wherein wherein said solution of bromine in chloroform is not radiated with radiation of a wavelength below 350 nm.

Preferably, the present invention relates to a process for preparing bromotrichloromethane comprising
  a) providing bromine in chloroform; and
  b) radiation of the resulting solution with light in the range of 350 to 550 nm,
wherein the irradiation source does not emit radiation below 350 nm.

Bromotrichloromethane is widely used, e.g. for chain transfer within radical polymerization of acrylate polymers (A. Matsumoto, K. Mizuta, Macromolecules 27 (1994) 5863) as bromination reagent for hydrocarbons (D. H. R. Barton, S. D. Bévière, W. Chavasiri, Tetrahedron 50 (1994) 31; T. Takahashi, K. Aoyagi and D. Y. Kondakov, J. Chem. Soc. Chem. Commun. (1994) 747; Earl S. Huyser J. Am. Chem. Soc., 82 (1960) 391) or in Corey-Fuchs- and Appel-reactions (S. G. Newman, C. S. Bryan, D. Perez, M. Lautens, Synthesis (2011) 342-346).

Bromotrichloromethane can also be starting material for complex organic molecules in the pharmaceutical or agricultural area.

There are various methods to prepare bromotrichloromethane described in prior art, however, they are quite unselective, require high energy consumption and are not atomefficent (see e.g. Comprehensive Organic Functional Group Transformations. Elsevier, 1995, S. 221, G. Lehmann, B. Lücke, J. prakt. Chem. 22 (1963) 230, K. Shigeki, K. Yoshitoku, T. Yasuo, JP19760125039 (1976), DE 1259318A).

Compared with these above-referred methodologies, photobromination should principally provide the advantage of a more selective methodology.

One example is the preparation bromotrichloromethane by photobromination using a 500 Watt-Mazda lamp, which was also used for heating the reaction mixture. E. G. Bohlman, J. E. Willard, J. Am. Chem. Soc. 64 (1942) 1342). A further approach to prepare bromotrichloromethane by photobromination with a quarz-mercury lamp at wavelength at 546 nm at temperatures in the range of 110-130° C. (V. Braunwarth, H.-J. Schumacher, Kolloidchemie 89 (1939) 184).

However, both approaches would, if applied in large-scale production lead to high energy costs and suffer, as shown below from poor selectivity.

Willard et al teaches photobromination in the presence of oxygen at wavelengths of 265 nm. Photobromination in the absence of oxygenat wavelengths at 365 nm or 313 nm was not successful (J. Willard, F. Daniels, *J. Am. Chem. Soc.* 57 (1935) 2240). However, oxygen in large scale production of bromotrichloromethane should be avoided, as this may lead to safety issues.

Thus, there is the need in the art for a process for atom-efficient large scale production of bromotrichlormethane. Furthermore, such process must have a high selectivity, wherein formation of unwanted by-products is reduced to minimal extent. Furthermore, such process must be also efficient in terms of energy.

Thus, the object of the present invention was to provide a process for atom-efficient large scale production of bromotrichlormethane with high selectivity, wherein formation of unwanted by-products is reduced to minimal extent, which is also efficient in terms of energy.

Surprisingly, it has been found that this objective has been achieved by a process for preparing bromotrichloromethane comprising
  a) providing bromine in chloroform; and
  b) radiation of the resulting solution with light in the range of 350 to 550 nm,
wherein said solution of bromine in chloroform is not radiated with radiation of a wavelength below 350 nm.

In one preferred embodiment, the present invention relates to a process for preparing bromotrichloromethane comprising
  a) providing bromine in chloroform; and
  b) radiation of the resulting solution with light in the range of 350 to 550 nm,
wherein the irradiation source does not emit radiation below 350 nm.

When it is stated herein that the reaction medium is not radiated with radiation of a wavelength below 350 nm, this shall be understood to mean that the reaction medium is not exposed to a significant amount, if any, of radiation of this wavelength from the source of radiation. In particular, this expression shall not be understood to mean that the reaction medium and the reaction product needs to be shielded against any UV radiation that may originate from solar radiation or other natural origin. UV radiation of natural origin, e.g. solar radiation, is not considered to be significant in this context.

The radiation is carried normally out in the range of 350 nm to 550 nm, preferably in the range of 380-550 nm, more preferably in the range of 390 to 490 nm.

In a preferred embodiment of the invention, the light emitted from the radiation source is monochromatic. The term "monochromatic light" means a symmetric mono-modal emission spectrum with halfwidth of +/−10-30 nm in relation to the wavelength of the emission maximum.

Suitable radiation sources are those known in the art.

Preferred radiation sources are light emitting diodes (LEDs) that emit light in the range of 350-550 nm, preferably in the range of 380-550 nm, more preferably in the range of 390 to 490 nm.

In one preferred embodiment, said solution of bromine in chloroform is not radiated with radiation of a wavelength above 550 nm. In one preferred embodiment, the radiation source does not emit radiation of a wavelength above 550 nm.

In this regard, it has to be noted, that radiation sources like doped mercury lamps that might be suitable at a first glance for photobromination to produce irradiation in the visible range emit in addition to radiation in the visible range also radiation below 350 nm. Thus, using these radiation sources, formation of by-products, such as bromodichloromethane occurs, which removal lead to yield losses, if these lamps are used as radiation sources without further measures like shielding the reaction vessel from such radiation, for example using a filter or a phosphor. Examples of suitable diodes are diodes emitting at 405, 420, 455, 470 and 485 nm (e.g. available from Seoul Viosys).

Chloroform as used in the industry comprises between 0.5 to 1.0% by weight of a stabilizer to absorb phosgene that can originate from oxidation of chloroform.

Currently used stabilizers are for example ethanol or amylene.

However, the presence of alcohols as stabilizer reduces or prevents satisfactory photobromination. The presence of alcohols in amounts above 0.5% by weight lead to lower yields and increased amounts of by-products. Thus, processes according to the invention are preferably carried out in the absence of alcohols, meaning that the amount of alcohols present in the reaction medium is below 0.5% by weight, based on the chloroform. Preferably, alcohol is present in amounts below 1000 ppm by weight, more preferably below 100 ppm and even more preferably below 10 ppm or 1 ppm, in each case weight ppm based on the chloroform. In one embodiment, the chloroform used does not comprise any alcohol. Chloroform in step b) must either comprise a different stabilizer (e.g. amylene) or any traces of alcohol must be removed prior to photobromination.

Alcohols means all alcohols principally suitable to prevent oxidation of chloroform, for example ethanol or other $C_1$-$C_6$ alcohols or $C_2$-$C_6$ diols.

Removal of the alcohol such as ethanol can be done using methods known in the art, e.g. distillation.

As mentioned above, in large scale production, the presence of oxygen is often unwanted. Thus, in a further embodiment of the invention the process according to the present is carried out in the absence of oxygen.

The reaction temperature can be in the range of −20° C. to 60° C., preferably in the range of +20 to 50° C.

The process according to the present invention can be carried out at a reaction pressure in the range of 0.1-20 bar. In a preferred embodiment, the reaction is carried out under atmospheric pressure.

The bromine present in step a) can be
i. directly added as bromine; or
ii. generated in situ.

For example, bromine can be generated from bromides by oxidation with e.g. bromites, bromates, perbromates or its corresponding acids or with $H_2O_2$.

In one preferred embodiment, elementary bromine is used in step a) in combination with bromates.

The bromine concentration in step a) is from 0.1 to 10% by weight.

The process of the present invention can be carried out continuously, wherein the consumed bromine is replaced and the produced hydrogenbromide and bromotrichloromethane are removed from the reaction mixture by extraction and/or distillation.

In one embodiment, a mixture of bromine and chloroform is pumped through a continuous flow reactor, followed by separation of the reaction product.

In a further embodiment of the present invention, the reaction is carried out in a two-phase system comprising water in addition to the organic phase. By replacement of the water phase, the by-product hydrogenbromide originating from the photobromination is transferred in the water phase and can be recycled by oxidation of the resulting bromide as described above. Alternatively, the reaction can be carried out batch-wise, wherein the concentration in the beginning is equal or less than 10% by weight and the reaction is stopped latest after full consumption of the bromine.

The invention is further illustrated, but not limited by the following examples:

EXAMPLES

The examples are carried out as described below at 20° C. under nitrogen atmosphere. Quantitative analysis of the resulting reaction mixture was carried out by gas-chromatography (Column: RTX-200-MS 30m). The chloroform used was stabilized with amylene and contained less than 0.5 wt % of ethanol.

Example 1

1% Bromine in Chloroform, 470 nm

A solution of 4,8 g (30,0 mmol) bromine in 477 g (4 mol) chloroform is radiated for 2 h by 100 LEDs' (wavelength 470 nm, 20° C.). Analysis of the resulting mixture revealed 4.8 g trichlorobromomethane (24.3 mmol, 81% yield).

Example 2

2% Bromine in Chloroform, 470 nm

A solution of 9.7 g (61 mmol) bromine in 477 g (4 mol) chloroform is radiated for 3 h by 100 LEDs' (wavelength 470 nm, 20° C.). Analysis of the resulting mixture revealed 10.7 g trichlorobromomethane (54 mmol, 89% yield).

Example 4

4% Bromine in Chloroform, 470 nm

A solution of 19.9 g (124.5 mmol) bromine in 477 g (4 mol) chloroform is radiated for 7 h by 100 LEDs' (wavelength 470 nm, 20° C.). Analysis of the resulting mixture revealed 20.4 g trichlorobromomethane (103 mmol, 83% yield).

Example 5

4% Bromine in Chloroform, 405 nm

A solution of 130 g (810 mmol) bromine in 3120 g (26 mol) chloroform is radiated for 3.5 h by 88 LEDs' (wavelength 405 nm, 20° C.). Analysis of the resulting mixture revealed 132.2 g trichlorobromomethane (667 mmol, 82%).

Example 6-24

Continuous Flow Reactor

A solution of bromine in chloroform was pumped through a photo continuous flow reactor at various temperature and flow rates, as shown in the following table. Samples of the resulting reaction mixtures were taken and analyzed by gas chromatography.

| Example | Temperature [° C.] | $Br_2$ in $CHCl_3$ [%] | Flow rate [g/h] | $CBrCl_3$ [g/h] | Yield [%] |
|---|---|---|---|---|---|
| 6 | 15 | 5.0 | 269.48 | 8.08 | 48.0 |
| 7 | 15 | 5.0 | 314.11 | 0.02 | 41.1 |
| 8 | 15 | 5.0 | 357.95 | 8.23 | 37.9 |
| 9 | 15 | 5.0 | 379.92 | 7.98 | 34.5 |
| 10 | 35 | 5.0 | 264.30 | 15.33 | 92.8 |
| 11 | 35 | 5.0 | 303.03 | 17.58 | 92.8 |
| 12 | 35 | 5.0 | 338.38 | 19.63 | 92.8 |
| 13 | 35 | 5.0 | 371.24 | 20.79 | 89.6 |
| 15 | 50 | 5.2 | 386.04 | 22.78 | 94.4 |
| 16 | 50 | 5.2 | 545.03 | 34.34 | 98.5 |
| 17 | 50 | 5.2 | 633.46 | 39.91 | 98.5 |
| 18 | 50 | 5.2 | 719.93 | 44.64 | 97.0 |
| 19 | 50 | 5.2 | 803.47 | 47.40 | 92.3 |

-continued

| Example | Temperature [° C.] | Br₂ in CHCl₃ [%] | Flow rate [g/h] | CBrCl₃ [g/h] | Yield [%] |
|---|---|---|---|---|---|
| 20 | 59 | 5.0 | 562.98 | 34.90 | 100.6 |
| 21 | 59 | 5.0 | 717.81 | 44.50 | 100.6 |
| 22 | 59 | 5.0 | 870.41 | 53.97 | 100.6 |
| 23 | 59 | 5.0 | 1038.42 | 63.34 | 99.0 |
| 24 | 59 | 5.0 | 1192.73 | 71.56 | 97.4 |

Example 25

Bromination with Br₂ and HBrO₃, 405 nm LED

A 2 l reaction vessel, equipped with a 405 nm LED photo closed loop reactor, is charged with 25 g (0.1564 mol) bromine dissolved in 1800 g chloroform. A solution of 11.8 g (0.0782 mol) sodium bromate in 75 g water and 7.67 g (0.04 mol) 50% H₂SO₄ is added. The biphasic system is stirred slowly at 25° C. The lower, organic phase is pumped for 7.25 h through the photo loop reactor and irradiated from 88 LEDs, emitting light at 405 nm. The reaction mixture gets colorless when conversion is completed. After separation of the two phases, the organic phase is analyzed by gas chromatography. 1826.9 g (4.2%, 75.63 g, 0.3814 mol, 97.6%) bromotrichloromethane are obtained.

Example 26

Bromination with Br₂ and HBrO₃, White LEDs

A 2 l reaction vessel, equipped with a LED lamp (720 Lumen), is charged with 10 g (0.0626 mol) bromine dissolved in 882 g chloroform. A solution of 4.72 g (0.0313 mol) sodium bromate in 60 g water and 3.07 g (0.0156 mol) 50% H₂SO₄ is added. The biphasic system is stirred vigorously at 30° C. and irradiated with a LED lamp, emitting white light. The reaction mixture gets colorless when conversion is completed. After separation of the two phases, the organic phase is analyzed by gas chromatography. 905.2 g (3.46%, 31.3 g, 0.158 mol, 100%) bromotrichloromethane are obtained.

Example 27

Bromination with HBr and HBrO₃, 470 nm LED

A 470 nm LED photo closed loop reactor, is charged with 259 g chloroform, a solution of 13.7 g (0.0906 mol) sodium bromate in 45 g water and 9.26 g (0.0906 mol) 96% H₂SO₄. 29.3 g (0.181 mol) 50% HBr is added within 30 min. The biphasic mixture is irradiated at 40° C. from 100 LEDs, emitting light at 470 nm. The reaction mixture gets colorless when conversion is completed. After separation of the two phases, the organic phase is analyzed by gas chromatography. 274.4 g (18.5 w %, 0.256 mol, 94.2%) bromotrichloromethane are obtained.

Comparative Examples

A solution of bromine in chloroform was irradiated a certain period of time with light from a medium pressure mercury lamp (TQ150Z2) or from monochromatic diodes as indicated below. Afterwards, a sample was taken, washed with aqueous sodium carbonate and measured by GC. The ratio chloroform/bromodichloromethane was calculated from the area % of each individual compound and is displayed in table 1 below:

TABLE 1

| No | w % Br2 | t (h) | λ (nm) | Ratio (BrCCl₃/BrCHCl₂) |
|---|---|---|---|---|
| 1* | 4 | 7 | 470 | 265 |
| 2* | 6 | 4 | 405 | >265 |
| 3** | 10 | 5 | TQ150Z2 | 3.8 |
| 4** | 2 | 7 | TQ150Z2 | 5.9 |

*according to the present invention
**comparative example

The results in table 1 show that high amounts of by-product bromodichloromethane (bp.: 90° C.) was produced, if medium pressure mercury lamp (TQ150Z2) was used as radiation source.

The invention claimed is:

1. A process for preparing bromotrichloromethane comprising
    a) providing a solution of bromine in chloroform; and
    b) radiation of the resulting solution with light in the range of 350 to 550 nm, wherein said solution of the bromine in the chloroform is not radiated with radiation of a wavelength below 350 nm.
2. The process of claim 1, wherein the light is a light-emitting diode.
3. The process of claim 1, wherein the wavelength of the radiation is in the range of 380 to 550 nm.
4. The process of claim 1, wherein the light is monochromatic.
5. The process of claim 1, wherein the process is carried out in the absence of oxygen.
6. The process of claim 1, wherein said process is carried out in the absence of alcohols.
7. The process of claim 1, wherein the light does not emit radiation below 350 nm.
8. The process of claim 1, wherein reaction temperature is from −20° C. to 60° C.
9. The process of claim 1, wherein reaction pressure is in the range of 0.1-20 bar.
10. The process of claim 1, wherein content of the bromine in the solution of the bromine in the chloroform in step a) is from 0.1 to 10% by weight.
11. The process of claim 1, wherein the bromine is generated in situ.
12. The process of claim 1, wherein the process is carried out under a nitrogen atmosphere.
13. The process of claim 5, wherein:
    reaction temperature is from −20° C. to 60° C.;
    reaction pressure is in the range of 0.1-20 bar; and
    content of the bromine in the solution of the bromine in the chloroform in step a) is from 0.1 to 10% by weight.

* * * * *